US00PP11884P2

(12) United States Plant Patent
Jessel, Jr.

(10) Patent No.: US PP11,884 P2
(45) Date of Patent: May 22, 2001

(54) CARNATION PLANT NAMED 'CFPC LACY'

(75) Inventor: Walter H. Jessel, Jr., Gonzales, CA (US)

(73) Assignee: California Florida Plant Co, LP, Salinas, CA (US)

( * ) Notice: Subject to any disclaimer, the term of this patent is extended or adjusted under 35 U.S.C. 154(b) by 0 days.

(21) Appl. No.: 09/181,006

(22) Filed: Oct. 28, 1998

(51) Int. Cl.[7] ..... A01H 5/00
(52) U.S. Cl. ..... Plt./273
(58) Field of Search ..... Plt./273, 272, 276, Plt./281

*Primary Examiner*—Bruce R. Campell
*Assistant Examiner*—Michelle Kizilkaya
(74) *Attorney, Agent, or Firm*—Christie, Parker & Hale, LLP

(57) ABSTRACT

A new variety of carnation plant producing yellow picotee purple flowers.

1 Drawing Sheet

BACKGROUND OF THE INVENTION

The present invention relates to a new and distinct variety of carnation plant which was originated by me in a controlled breeding program by my crossing as seed parent an unnamed, undistributed seedling identified as No. 950192 and as pollen parent an unnamed and undistributed seedling identified as No. 950024. The varietal denomination of the new variety is 'CFPC Lacy'.

SUMMARY OF THE INVENTION

Among the novel characteristics possessed by the new variety which distinguishes it is flowers of yellow picotee purple color. When grown under glass in Salinas, Calif., pinched plants are about 7 inches tall and about 7 inches whide in a 4½ inch plastic pot. Flower diameter averages about 2 inches with a crown of about 1 inch (average). Foliage is about 3¼ inches long and about 7/16 inches wide. The new plant varies from the undistributed parent plants in that the seed parent, No. 950192 and the pollen parent, No. 950024 differ in size and vigor.

Asexual reproduction by propagation by side shoot cuttings of the new variety as performed in Salinas, Calif., shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety depicted in color as nearly true as it is reasonably possible to make the same in color illustration of this character.

DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart. Phenotypical expression may vary depending upon varying environmental, seasonal and cultural conditions.

The information provided herein is based on observations of plants grown inside commercial greenhouses at Salinas, Calif. The height of plant and flower and foliage size are established as an average using standard commercial cultural parctices.

Classification:
*Botanical.*—*Dianthus caryophyllus.*
*Commercial.*—Carnation, greenhouse type, suitable for production as a pot spray.

1. Plant:
*Height.*—About 7 inches.
*Growing habit.*—Herbaceous, semi-upright.
*Blooming habit.*—As a spray (pot), about 2 to 3 blooms per spray.
*Blooming season.*—Year round.
*Breaking action.*—Good, averages about 15 breaks per plant, pinching is required.
*Rooting time.*—About 18 days.
*Disease resistance.*—Good, typical of carnations.

2. Foliage:
*Color.*—Upper side: Near 136B. Lower side: Near 137B.
*Size.*—About 3¼ long, 7/16 inches wide.
*Quantity.*—Numerous.
*Shape.*—Lanceolate.
*Texture.*—Smooth.
*Ribs.*—Central, keeled.
*Arrangement.*—Bi-lateral along stem.
*Stem color.*—Near 135A at maturity.
*Pedicel.*—Near 135A.
*Lastingness.*—About 1 week after cutting.

3. Bud:
*Shape.*—Ovoid.
*Color.*—Near 138C.
*Length.*—About 1 inch.
*Diameter.*—About 7/16 inch.

4. Calyx:
*Number of bracts.*—About 5.
*Length.*—About ¼ inch.
*Width.*—About ¼ inch.
*Color.*—Outside — 138C. Inside — 147C.
*Bursting/splitting.*—Has not been observed.

5. Bloom:
*Shape.*—Round.
*Size.*—Diameter average: About 2 inches. Depth average: About 1 inch.
*Borne.*—As a spray.

*Color*.—General tonality: Yellow picotee purple. Upper side: Near 8C. Lower side: Near 8D. Center: Near 8C. Petal margins: Near 60B.

*Keeping quality*.—Very good, 3 plus weeks.

*Fragrance*.—Slight.

6. Petals:

*Number*.—About 25–26 average.

*Outer petals*.—Length: About 1 9/16 inches. Width: About 1 inch.

*Central petals*.—Length: About 1½ inches. Width: About ¾ inch.

*Texture*.—Smooth.

*Form*.—Fan shaped.

*Appearance*.—Shiny.

*Margin*.—Smooth.

7. Reproductive organs:

*Stamens*.—None (male sterile).

*Pistil*.—Number: 1. Color: whiter than 155D. Length: About 15/16 inches.

*Stigma*.—Number: About 2 (bilobed). Color: Whiter than 155D.

*Ovary*.—Shape: Conical. Color: Base — near 155D. Body — near 147C. Apex — near 147C.

*Fertility*.—Female: Good. Male: None.

I claim:

1. A new and distinct carnation plant of the variety substantially as shown and described.

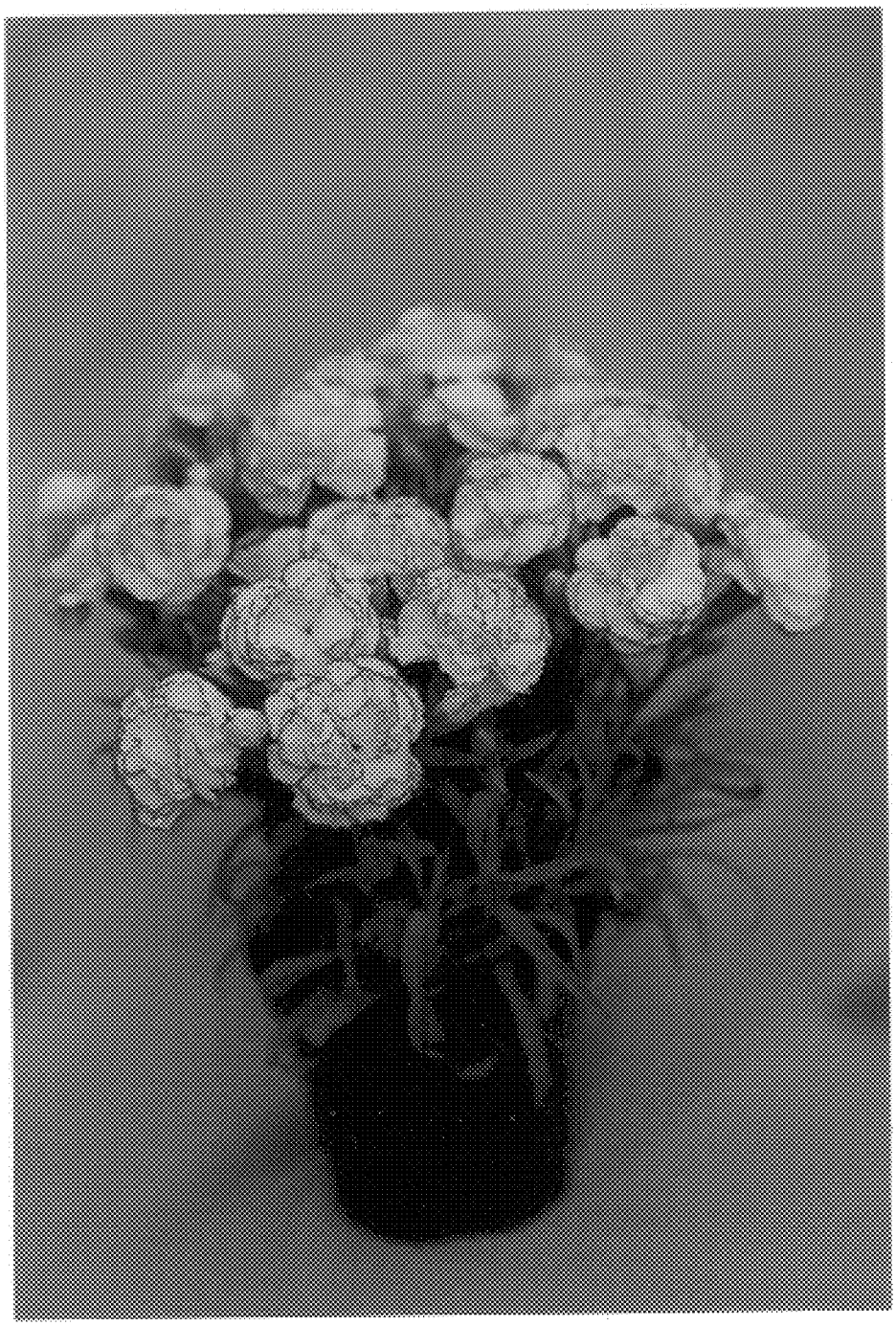

* * * * *